(12) United States Patent
Hodde et al.

(10) Patent No.: US 8,784,889 B2
(45) Date of Patent: Jul. 22, 2014

(54) GRAFT WITH INCREASED RESISTANCE TO ENZYMATIC DEGRADATION

(75) Inventors: Jason P. Hodde, West Lafayette, IN (US); David M. J. Ernst, Lafayette, IN (US)

(73) Assignee: Cook Biotech Incorporated, West Lafayette, IN (US)

( * ) Notice: Subject to any disclaimer, the term of this patent is extended or adjusted under 35 U.S.C. 154(b) by 1815 days.

(21) Appl. No.: 11/668,908

(22) Filed: Jan. 30, 2007

(65) Prior Publication Data

US 2007/0122390 A1    May 31, 2007

Related U.S. Application Data

(63) Continuation of application No. PCT/US2005/027142, filed on Jul. 29, 2005.

(60) Provisional application No. 60/593,002, filed on Jul. 30, 2004.

(51) Int. Cl.

| | |
|---|---|
| *A61K 9/00* | (2006.01) |
| *A61L 27/36* | (2006.01) |
| *A61K 35/22* | (2006.01) |
| *A61K 35/42* | (2006.01) |
| *A61K 35/38* | (2006.01) |

(52) U.S. Cl.
CPC ......... *A61L 27/3687* (2013.01); *A61L 27/3633* (2013.01); *A61K 35/22* (2013.01); *A61K 35/42* (2013.01); *A61L 27/3641* (2013.01); *A61L 27/3629* (2013.01); *A61K 35/38* (2013.01)
USPC ........................................................ 424/484

(58) Field of Classification Search
CPC ... A61K 2300/00; A61K 38/00; A61K 35/12; A61K 38/39; A61K 35/50; A61K 35/48; A61K 9/0024; A61K 9/006; A61F 2/2418; A61F 2/06; A61F 2/0063; A61F 2/02; A61F 2/08
See application file for complete search history.

(56) References Cited

U.S. PATENT DOCUMENTS

| | | | |
|---|---|---|---|
| 2,127,903 | A | 8/1938 | Bowen |
| 4,902,508 | A | 2/1990 | Badylak et al. |
| 4,956,178 | A | 9/1990 | Badylak et al. |
| 4,976,733 | A | 12/1990 | Girardot |
| 5,275,826 | A | 1/1994 | Badylak et al. |
| 5,281,422 | A | 1/1994 | Badylak et al. |
| 5,372,821 | A | 12/1994 | Badylak et al. |
| 5,447,536 | A | 9/1995 | Girardot et al. |
| 5,516,533 | A | 5/1996 | Badylak et al. |
| 5,554,389 | A | 9/1996 | Badylak et al. |
| 5,641,518 | A | 6/1997 | Badylak et al. |
| 5,993,844 | A | 11/1999 | Abraham et al. |
| 6,099,567 | A | 8/2000 | Badylak et al. |
| 6,206,931 | B1 | 3/2001 | Cook et al. |
| 6,235,494 | B1 * | 5/2001 | Hugli .............................. 435/24 |
| 2003/0036636 | A1 | 2/2003 | Huang et al. |

FOREIGN PATENT DOCUMENTS

| | | |
|---|---|---|
| WO | WO 89/06945 | 8/1989 |
| WO | WO 96/32146 | 10/1996 |
| WO | WO 02/32474 A1 | 4/2002 |
| WO | WO 03/064706 A1 | 8/2003 |
| WO | WO 2005/020847 A3 | 3/2005 |

OTHER PUBLICATIONS

Yu, Sumei et al., "Comparative Study of the Protease Digestion of No-React™ and Conventional Glutaraldehyde Treated Bioprosthetic Heart Valves," Bioengineering Conference, 1996, *Proceedings of the 1996 IEEE Twenty-Second Annual Northeast*, New Brunswick, New Jersey, Mar. 14-15, 1996; *IEEE*, New York, New York, Mar. 14, 1996, pp. 84-86.

* cited by examiner

*Primary Examiner* — Lora E Barnhart Driscoll
(74) *Attorney, Agent, or Firm* — Woodard, Emhardt, Moriarty, McNett & Henry LLP

(57) ABSTRACT

Described are devices, methods, and systems for grafting tissues or organs that are exposed to bacterial or mammalian enzymes that degrade collagenous materials. Illustrative medical grafts are processed by contacting a collagenous extracellular matrix (ECM) material with a mono-carboxylic acid having from four to about twelve carbon atoms, or mixtures of two or more such acids.

7 Claims, No Drawings

GRAFT WITH INCREASED RESISTANCE TO ENZYMATIC DEGRADATION

CROSS REFERENCE TO RELATED APPLICATIONS

This application is a continuation of International Patent Application Serial No. PCT/US2005/027142 filed Jul. 29, 2005 (published in English), which claims the benefit of U.S. Provisional Patent Application Ser. No. 60/593,002 filed Jul. 30, 2004, both of which are incorporated herein by reference in their entirety.

BACKGROUND

The present invention relates generally to medical graft products that exhibit increased resistance to enzymatic breakdown. One aspect of the present invention provides an extracellular matrix (ECM) material treated with an agent that increases its resistance to digestive enzymes such as pepsin while allowing the ECM to retain beneficial grafting properties.

As further background, extracellular matrix materials, including submucosa, are known medical graft materials. See, e.g., U.S. Pat. Nos. 4,902,508, 4,956,178, 5,281,422, 5,372,821, 5,554,389, 5,993,844, 6,099,567, and 6,206,931. As taught in these patents, submucosa from various biological structures such as small intestine, stomach, and the urinary bladder provide predominantly collagenous materials useful in a variety of surgical procedures where tissue support and/or ingrowth are desired.

U.S. Pat. No. 4,976,733 to Girardot teaches the covalent coupling of aliphatic carboxylic acids having from about eight to about thirty carbon atoms to a prosthesis before implantation in a mammal in order to retard or prevent calcification of the prosthesis. The prosthesis materials disclosed include natural tissue, porcine heart valve tissues, and urinary tract and bladder replacements.

U.S. Pat. No. 5,447,536 to Girardot et al. teaches fixation agents for biological tissue that may include di- or tri-carboxylic acids having about six to about eight carbon atoms. The fixation process creates amide linkages between and within the molecules of the biological tissue thereby producing tissues resistant to calcification. In addition, the resulting tissue is not toxic and does not elicit inflammatory responses after implantation. The prosthesis materials disclosed include natural tissue, porcine heart valve tissues, and urinary tract and bladder replacements.

In view of the above background, there remain needs for improved or alternative medical graft products; especially graft products that are resistant to enzymatic degradation. The present invention is addressed to those needs.

SUMMARY OF INVENTION

In one embodiment, the invention provides a medical grafting product that exhibits increased resistance to enzymatic break down. The product includes an extracellular matrix (ECM) material treated with an agent that increases its resistance to a digestive enzyme, such as pepsin. Advantageous such products include ECM materials that are treated with a mono-carboxylic acid having from four to about twelve carbon atoms, or mixtures of two or more of such acids.

In another embodiment, the invention provides a medical graft composition that includes submucosa of a warm-blooded vertebrate treated with octanoic acid so as to increase its resistance to a digestive enzyme.

In another embodiment, the invention provides a planar graft construct configured to form a large surface area graft by combining two or more ECM segments of the invention that are partially overlapped and bonded to one another. The planar graft construct can be treated with a mono-carboxylic acid to increase its resistance to enzymatic degradation.

In another embodiment, the invention provides multi-layered grafts including two or more ECM segments in partially or completely overlapping relationship. Sections, layers, and/or portions of each layer of the multi-layered graft, or the entire graft construct, can be treated with a mono-carboxylic acid to increase resistance to enzymatic degradation.

In another embodiment, the invention provides single or multiple layered tubular medical graft constructs that may for example be used to graft in the gastrointestinal tract. The tubular graft treated with a mono-carboxylic acid to increase resistance of those portions to enzymatic degradation.

The present invention provides improved and/or alternative medical ECM graft products. These medical graft products include for example large area grafts, multi-layer grafts, and tubular grafts. The invention also provides manufacturing and grafting methods involving such medical graft products. Additional embodiments and features and advantages of the invention will be apparent from the descriptions herein.

DETAILED DESCRIPTION

For the purposes of promoting an understanding of the principles of the invention, reference will now be made to certain embodiments thereof and specific language will be used to describe the same. It will nevertheless be understood that no limitation of the scope of the invention is thereby intended, such alterations, further modifications and further applications of the principles of the invention as described herein being contemplated as would normally occur to one skilled in the art to which the invention relates.

As disclosed above, the present invention provides a medical graft product that includes a collagenous extracellular matrix material treated with a mono-carboxylic acid. The product, in its preferred form, is both biotropic and will resist degradation from digestive enzymes. The invention also provides grafting methods utilizing such medical graft products, and particularly advantageous methods involve grafting in the gastrointestinal tract or other organs or tissues that may be exposed to digestive enzyme(s). The invention also provides methods of manufacturing such collagenous extracellular matrix materials, and medical articles that include such materials enclosed within sterile packaging.

The medical graft products of the invention will include collagenous extracellular matrix, such as submucosa, renal capsule membrane, dura mater, pericardium, serosa, peritoneum, or basement membrane. The preferred medical graft products of the invention will include submucosa, such as submucosa derived from a warm-blooded vertebrate. Mammalian submucosa materials are preferred. In particular, submucosa materials derived from animals raised for meat or other product production, e.g. pigs, cattle or sheep, will be advantageous. Porcine submucosa provides a particularly preferred material for use in the present invention, especially porcine small intestine submucosa.

The submucosa or other ECM material can be derived from any suitable organ or other biological structure, including for example submucosa derived from the alimentary, respiratory, intestinal, urinary or genital tracts of warm-blooded vertebrates. Submucosa useful in the present invention can be obtained by harvesting such tissue sources and delaminating the submucosa from smooth muscle layers, mucosal layers, and/or other layers occurring in the tissue source. For additional information as to submucosa useful in the present invention, and its isolation and treatment, reference can be made, for example, to U.S. Pat. Nos. 4,902,508, 5,554,389, 5,993,844, 6,206,931, and 6,099,567.

As prepared, the extracellular matrix (ECM) material may optionally retain growth factors or other bioactive components native to the source tissue. For example, the matrix material may include one or more growth factors such as basic fibroblast growth factor (FGF-2), transforming growth factor beta (TGF-beta), epidermal growth factor (EGF), and/or platelet derived growth factor (PDGF). As well, submucosa or other ECM material of the invention may include other biological materials such as heparin, heparin sulfate, hyaluronic acid, fibronectin and the like. Thus, generally speaking, the ECM material may include a bioactive component that induces, directly or indirectly, a cellular response such as a change in cell morphology, proliferation, growth, protein or gene expression. Further, in addition or as an alternative to the inclusion of such native bioactive components, non-native bioactive components such as those synthetically produced by recombinant technology or other methods, may be incorporated into the ECM material.

ECM material used in the invention is preferably highly purified, for example, as described in U.S. Pat. No. 6,206,931. Thus, preferred material will exhibit an endotoxin level of less than about 12 endotoxin units (EU) per gram, more preferably less than about 5 EU per gram, and most preferably less than about 1 EU per gram. As additional preferences, the ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 µg/mg, more preferably less than about 2 µg/mg, and virus levels are preferably less than about 50 plate forming units (PFU) per gram, more preferably less than about 5 PFU per gram. The ECM material used in certain embodiments of the invention is preferably disinfected with an oxidizing agent, particularly a peracid, such as peracetic acid. These and additional properties of submucosa tissue taught in U.S. Pat. No. 6,206,931 may be characteristic of the ECM material used in the present invention.

In accordance with the invention, the ECM material will be processed so as to increase its resistance to degradation by one or more enzymes. Such enzymatic resistance can be accomplished by contacting the ECM material with a mono-carboxylic acid. Preferred mono-carboxylic acids are those containing from one to about twelve carbon atoms, including those having an aliphatic hydrocarbon group having one to eleven carbon atoms, such group being attached to a carboxylic acid (—COOH) group. Preferred acids for use in the invention exhibit the following structure wherein n ranges from two to ten.

$$CH_3(CH_2)_nCO_2H$$

Preferred acids, thus include butanoic, pentanoic, hexanoic, heptanoic, octanoic, nonanoic, decanoic, undecanoic, and/or dodecanoic acid, or mixtures of two or more of these acids.

The medical graft product of this invention is prepared by contacting an ECM material with any of the aforementioned mono-carboxylic acids or any mixtures thereof. Any suitable means of contacting the ECM material with the mono-carboxylic acid will suffice, including for instance spray contacting and/or contacting through submersion or soaking. When treating the ECM material, any suitable acid-containing medium may be used, such as a solution or suspension. Additionally any suitable acid carrier may also be used, such carrier being preferably liquid, more preferably aqueous, such as an aqueous ethanol solution, for example.

Preferred aqueous acids will have a concentration of about 0.05% to about 1%, more preferably a concentration of about 0.1% to about 0.4%, and most preferably a concentration of about 0.2% to about 0.3%. In methods of the present invention, the carboxylic acid will generally be in contact with the ECM material for any suitable time to achieve the desired increase in resistance to enzymatic degradation. In this regard, desirable processes of the invention involve contacting the source ECM material (e.g. by submersion or showering) in a liquid medium containing the mono-carboxylic acid for a period of at least about five minutes, typically in the range of about five minutes to about 40 hours, and more typically in the range of about 0.5 hours to about five hours.

After treating the ECM material with a mono-carboxylic acid, the graft material can be rinsed with water. Rinsing of the graft material can occur by contacting or spraying the graft material for a period of at least about five minutes, typically in the range of about five minutes to about five hours, and more typically in the range of about 0.5 hours to about two hours. After rinsing is complete, the entire medical graft product may be dried (e.g. lyophilized) or otherwise processed prior to use.

The invention also encompasses medical products including a graft material of the invention sealed within sterile medical packaging. The final, packaged product is provided in a sterile condition. This may be achieved, for example, by gamma, e-beam or other irradiation techniques, ethylene oxide gas, or any other suitable sterilization technique, and the materials and other properties of the medical packaging will be selected accordingly. The prosthesis device may be packaged wet (e.g. suspended in aqueous solution) or dried.

Graft materials in accordance with the present invention can be used to graft mammalian patients, including humans. Preferred graft materials of the invention find particular utility in repairing areas of the body that are subject to enzymatic digestion. For example, graft materials of the invention are used with preference in gastrointestinal tract applications, such as repairing the esophagus, stomach, intestine (including large and small intestine), the mouth and/or palate, and other gastrointestinal tract components.

Treated graft materials of the invention can be resistant to enzymatic degradation by bacterial and/or mammalian enzymes. Illustrative such enzymes can include aspartyl proteases, such as pepsin; extracellular matrix proteases; matrix metalloproteases; serine proteases; other enzymes released by pathogenic bacteria; other digestive enzymes; and/or the like.

Graft materials according to the present invention may be processed in a numbers of ways, to provide ECM materials suitable for use in a variety of grafting needs. Illustrative such processing methods are taught in U.S. Pat. No. 6,206,931. For example, the ECM materials may be configured to form large surface area grafts by combining two or more ECM segments of the invention, for instance using techniques as described in U.S. Pat. No. 2,127,903 and/or International Publication No. WO96/32146, dated Oct. 17, 1996, publishing International Application No. PCT/US96/04271, filed Apr. 5, 1996. Thus, a plurality of ECM strips can be fused to one another, for example by compressing overlapping areas of the strips under dehydrating conditions, to form an overall planar graft having a surface area greater than that of any one planar surface of the individual strips used to form the graft.

The large surface area grafts described above can be treated in a plurality of ways with an aforementioned carboxylic acid, or any mixture thereof in order to selectively increase the resistance of the treated area to enzymatic degradation. One method of treating the large surface area graft is to treat each ECM strip before assembling the large graft. A second method of treating the large surface area graft is to treat the entire graft after it has been assembled. In either treating method, any portion of either side of the graft material may be selectively treated, or, alternatively, any portion of only one side of the graft material may be selectively treated with an aforementioned mono-carboxylic acid or any mixture thereof.

It is also possible to form layered or multi-layered grafts by combining two or more ECM segments of the invention, with at least the opposite end portions and/or opposite lateral portions being formed to have multiple layers of the graft material to provide reinforcement for attachment to physiological structures such as cartilage and muscle. Additionally, multi-laminate grafting materials can be formed by stacking two or more ECM segments or by folding one ECM segment over itself at least one time, and then fusing or bonding the overlapped layers together using a bonding technique, such as chemical cross-linking or compressing the layered materials during dehydrating conditions. Treatments with mono-carboxylic acids in accordance with the invention can occur, for example, before and/or after such layering techniques.

The multi-layered grafts described above can be treated in a plurality of ways with an aforementioned carboxylic acid, or any mixture thereof in order to selectively increase the resistance of the treated area to enzymatic degradation. One method of treating a multi-layered graft is to treat each ECM strip before assembling the large graft. A second method of treating the multi-layered graft is to treat the entire graft after it has been assembled. In either treating method, any portion of any side of the graft material may be selectively treated, or, alternatively, any portion of only one side of the graft material may be selectively treated with an aforementioned mono-carboxylic acid or any mixture thereof.

In another example, treated ECM material can be processed into single or multiple layered tubular structures that are used as medical graft materials in the gastrointestinal tract. In illustrative preparative procedures, the graft is formed over a sterile rod or mandrel having an outer diameter approximately equal to that of the tube to be grafted. For instance, the rod is introduced into the lumen of an ECM material segment retaining its native, tubular form. Redundant ECM material is then gathered, and the desired lumen diameter achieved by suturing along the length of the graft (for example, using two continuous suture lines or a simple interrupted suture line), or by using other art-recognized ECM material securing techniques. Alternatively, a sheet of the inventive ECM material is wrapped about the rod to form an overlapping seam, which can be sutured, glued, or otherwise secured, to provide the tubular graft material. In preferred forms, the inner, luminal surface of the graft can be formed by the mucosal side of the ECM material.

The single or multi-layered tubular grafts described above can be treated in a plurality of ways with an aforementioned carboxylic acid, or any mixture thereof in order to selectively increase the resistance of the treated area to enzymatic degradation. One method of treating the single or multi-layered tubular graft is to treat each ECM material before assembling the large graft. A second method of treating the single or multi-layered tubular graft is to treat the entire graft after it has been assembled. In either treating method, any portion of any side of the graft material may be selectively treated, or, alternatively, any portion of only one side of the graft material may be selectively treated with an aforementioned mono-carboxylic acid or any mixture thereof.

In still further applications, treated extracellular matrix tissue of the invention can be provided in any three-dimensional shape configured for implant in the patient, for example in the gastrointestinal tract. As well, the treated extracellular matrix material can be used alone, or in combination with one or more additional bioactive agents such as physiologically compatible minerals, growth factors, antibiotics, chemotheraputic agents, antigen, antibodies, enzymes and hormones.

In certain embodiments, graft materials of the invention can be provided as particulate form ECM materials, e.g. powders. The particulate form ECM material can be implanted into a damaged or diseased tissue region to facilitate the repair of that region. The ECM particulate material can be used alone, or in combination with one or more additional bioactive agents, as discussed above. In certain embodiments, the powder or particulate form ECM material can be compressed into a predetermined three-dimensional shape which will be implanted into a patient and will substantially retain its shape during remodeling of the graft with endogenous patient tissue. For more information concerning particulate form materials, reference can be made, for example, to U.S. Pat. Nos. 5,641,518 and/or 6,206,931.

Additionally, graft materials of the invention can include a flowable remodelable extracellular matrix material. Suitable techniques involved in preparing flowable, remodelable ECM materials are described for example in U.S. Pat. Nos. 5,275,826 and 5,516,533 or in International Publication No. WO2005020847 (Cook Biotech Incorporated) published Mar. 10, 2005, which are each hereby incorporated by reference in their entirety. In certain forms, such flowable materials can include solubilized and/or particulate ECM components treated with a monocarboxylic acid as described herein, and in preferred forms include ECM gels having suspended therein ECM particles treated with the mono-carboxylic acid, for example having an average particle size of about 50 microns to about 500 microns, more preferably about 100 microns to about 400 microns. Such particles can be prepared by treating a larger ECM material with the mono-carboxylic acid, and then reducing the material to a particulate. In one preferred form, the ECM material is treated with the mono-carboxylic acid after it is reduced to particulate form. Combinations of these treatment techniques may also be used. The ECM particulate can be added in any suitable amount relative to solubilized ECM components, with preferred ECM particulate to ECM solubilized component weight ratios (based on dry solids) being about 0.1:1 to about 200:1, more preferably in the range of 1:1 to about 100:1. The inclusion of such ECM particulates in the ultimate gel can serve to provide additional material that can function to provide bioactivity to the gel (e.g. itself including FGF-2 and/or other growth factors or bioactive substances) and/or serve as scaffolding material for tissue ingrowth.

Flowable ECM materials can be pre-formed into shape retaining three-dimensional constructs for delivery to an implant location, or alternatively, flowable ECM material can be delivered or injected into an implant location in a flowable form and potentially thereafter solidify into a rigid or semi-rigid volumetric implant, upon a change in pH or temperature, for example, as is discussed in International Publication No. WO2005020847.

Three-dimensional grafts described above can be treated in a plurality of ways with an aforementioned carboxylic acid, or any mixture thereof in order to selectively increase the resistance of the treated area to enzymatic degradation. One method of treating the three-dimensional graft is to treat any portion of multiple sides of the graft material. A second method of treating the three-dimensional graft is to selectively treat only one side, or only a portion of one side of the graft, while leaving the other side or sides untreated.

For the purpose of promoting a further understanding of the present invention and its features and advantages, the following specific examples are provided. It will be understood that these examples are illustrative, and not limiting, of the invention.

Example 1

A section of porcine small intestinal submucosa was rinsed, split open, and then contacted in a 0.25% octanoic acid solution in 5% ethanol for a period of two hours. The small intestinal submucosa layer was then removed from the solution and rinsed using four, 15-minute exchanges of sterile water.

Example 2

A portion of small intestinal submucosa treated according to Example 1 was placed in a solution containing 0.2M acetic acid and 0.1% pepsin for a period of 24 hours at room temperature. At the end of the 24-hour period, the small intestinal submucosa piece was removed from the pepsin solution and was found to be intact, thus demonstrating significantly increased resistance to pepsin degradation as compared to untreated small intestinal submucosa.

Example 3

A section of peracetic acid disinfected small intestine submucosa (SIS) (prepared generally as described in U.S. Pat. No. 6,206,931) was divided into equal halves. One half of the material was treated with a solution of 5% ethanol for 2 hours at room temperature, then rinsed in 4 exchanges of water. The other half of the material was treated with 0.25% octanoic acid in 5% ethanol for 2 hours at room temperature, and then rinsed in 4 exchanges of water. Both sections of treated SIS were stored overnight at 4 degrees celcius.

The treated samples were then cut into 1×7 cm strips and submerged under tension in a fluid bath containing 0.05 mM Tris-HCl/10 mM CaCl2 buffer (pH 7.4) with a collagenase concentration of 1 mg/ml. The time taken for the strip to break was then recorded using an automated system controlled by a computer.

This experiment was repeated 3 times on three separate lots of SIS material.

The average time to failure in the collagenase-containing bath was 4.41+/−0.54 hours for the untreated material and 5.99+/−0.72 hours for the octanoic acid treated material (p<0.001, 2-tailed t-test), indicating that octanoic acid treatment of SIS increases the resistance of the SIS material to enzymatic degradation by the collagenase enzyme.

All publications cited herein are hereby incorporated by reference in their entirety as if each had been individually incorporated by reference and fully set forth.

While the invention has been illustrated and described in detail in the foregoing description, the same is to be considered as illustrative and not restrictive in character, it being understood that only the preferred embodiments have been shown and described and that all changes and modifications that come within the spirit of the invention are desired to be protected.

What is claimed is:

1. A method for preparing a medical graft product, comprising:
   contacting an extracellular matrix material retaining growth factors or other bioactive components native to a source tissue for the extracellular matrix material with a mono-carboxylic acid having from four to twelve carbon atoms in an amount effective to increase resistance of the extracellular matrix material to degradation caused by enzymes relative to an untreated extracellular matrix material.

2. The method of claim 1, wherein said extracellular matrix material comprises submucosa.

3. The method of claim 2, wherein said submucosa comprises small intestinal submucosa.

4. The method of claim 3, wherein said small intestinal submucosa is porcine.

5. The method claim of 4, wherein said small intestinal submucosa is bioremodelable.

6. The method claim of 5, wherein said mono-carboxylic acid comprises octanoic acid.

7. The method of claim 1, wherein said mono-carboxylic acid comprises butanoic, pentanoic, hexanoic, heptanoic, octanoic, nonanoic, decanoic, hendecanoic, dodecanoic acid, or any mixtures of two or more of these acids.

* * * * *